(12) United States Patent
Werner

(10) Patent No.: US 12,082,786 B2
(45) Date of Patent: Sep. 10, 2024

(54) MODULE FOR APPLYING A MEDIUM TO ITEMS TO BE WASHED

(71) Applicant: Miele & Cie. KG, Guetersloh (DE)

(72) Inventor: Alexander Werner, Bielefeld (DE)

(73) Assignee: MIELE & CIE. KG, Guetersloh (DE)

( * ) Notice: Subject to any disclaimer, the term of this patent is extended or adjusted under 35 U.S.C. 154(b) by 0 days.

(21) Appl. No.: 18/562,344

(22) PCT Filed: May 10, 2022

(86) PCT No.: PCT/EP2022/062603
§ 371 (c)(1),
(2) Date: Nov. 20, 2023

(87) PCT Pub. No.: WO2022/243108
PCT Pub. Date: Nov. 24, 2022

(65) Prior Publication Data
US 2024/0237890 A1    Jul. 18, 2024

(30) Foreign Application Priority Data
May 21, 2021   (DE) .................. 10 2021 113 274.6

(51) Int. Cl.
*A61B 1/12*     (2006.01)
*B08B 9/02*     (2006.01)
(Continued)

(52) U.S. Cl.
CPC ................ *A61B 1/125* (2013.01); *B08B 9/02* (2013.01); *B08B 9/027* (2013.01); *B08B 9/032* (2013.01); *A61B 1/12* (2013.01)

(58) Field of Classification Search
CPC .. A61B 1/12; A61B 1/125; B08B 9/02; B08B 9/027; B08B 9/032
See application file for complete search history.

(56) References Cited

U.S. PATENT DOCUMENTS

2010/0266447 A1   10/2010   Medici

FOREIGN PATENT DOCUMENTS

DE   102017112169 B3 *  7/2018  ............. A61B 90/70
DE   102018121450 A1     3/2020
(Continued)

OTHER PUBLICATIONS

Machine Translation of DE 102017112169 B3 to Aehlig. (Year: 2018).*
Machine Translation of WO 2018219571 A1 to Aehlig. (Year: 2018).*

*Primary Examiner* — Benjamin L Osterhout
(74) *Attorney, Agent, or Firm* — LEYDIG, VOIT & MAYER, LTD.

(57) ABSTRACT

A module for applying a medium to narrow-bore ducts, conduits, pipes, and/or the like, of items to be washed, in particular endoscopes, which are disposed in a wash tub of a cleaning device, the module including: a medium distribution device having a plurality of inlet-side ports and outlet-side ports, the inlet-side ports being in fluid connection with the outlet-side ports; and a carrier flange having a push-pull cylinder, the push-pull cylinder being in fluid connection with an inlet-side port, and the push-pull cylinder providing a piston rod which is provided at an end thereof with an anchor that cooperates with a connecting device of a carrier for items to be washed.

20 Claims, 9 Drawing Sheets

(51) Int. Cl.
*B08B 9/027* (2006.01)
*B08B 9/032* (2006.01)

(56) References Cited

FOREIGN PATENT DOCUMENTS

| | | | |
|---|---|---|---|
| EP | 0709056 | A1 | 5/1996 |
| EP | 1253951 | A2 | 11/2002 |
| EP | 3005936 | A1 | 4/2016 |
| WO | WO-2018219571 | A1 * | 12/2018 ............. A61B 90/70 |

\* cited by examiner

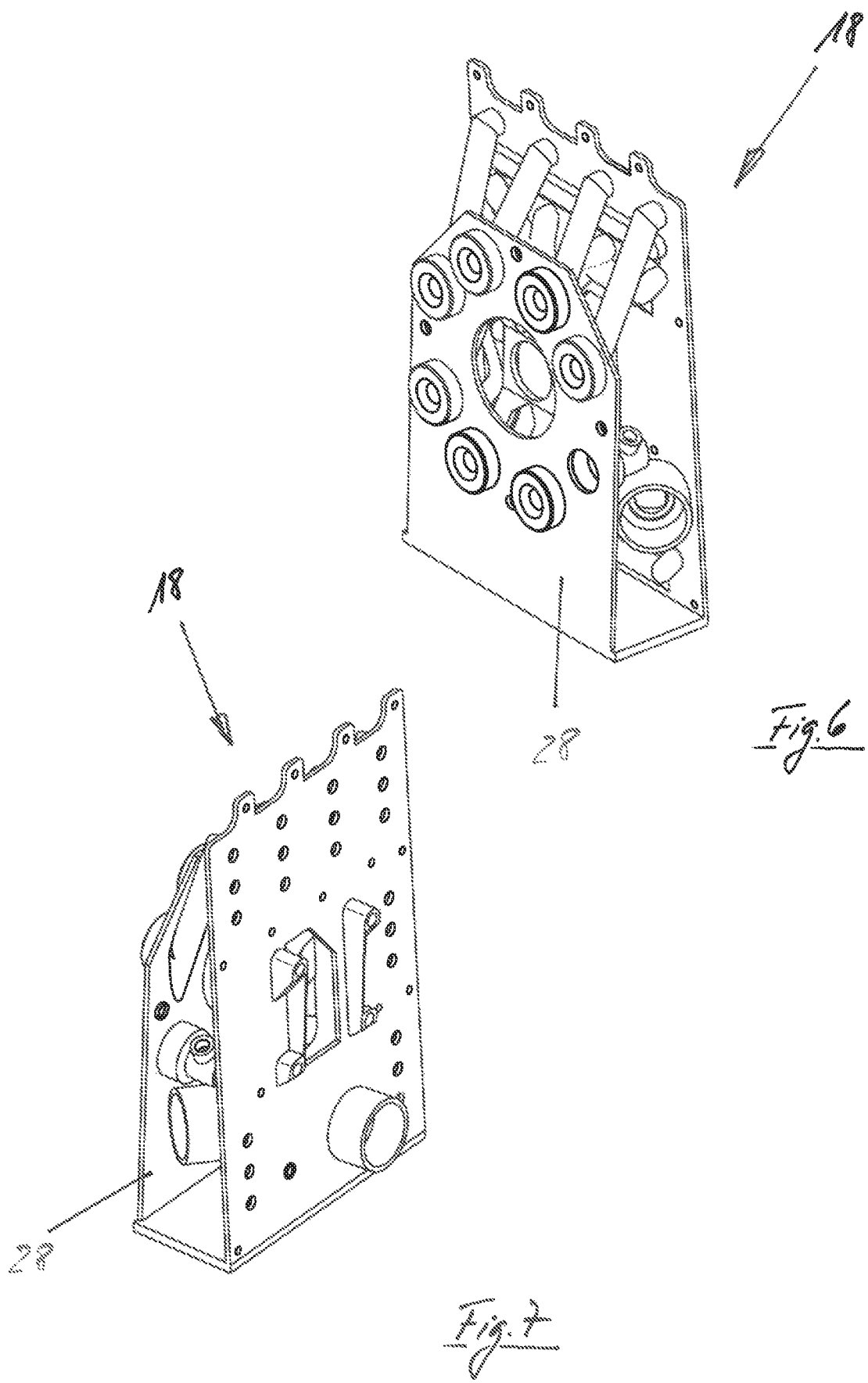

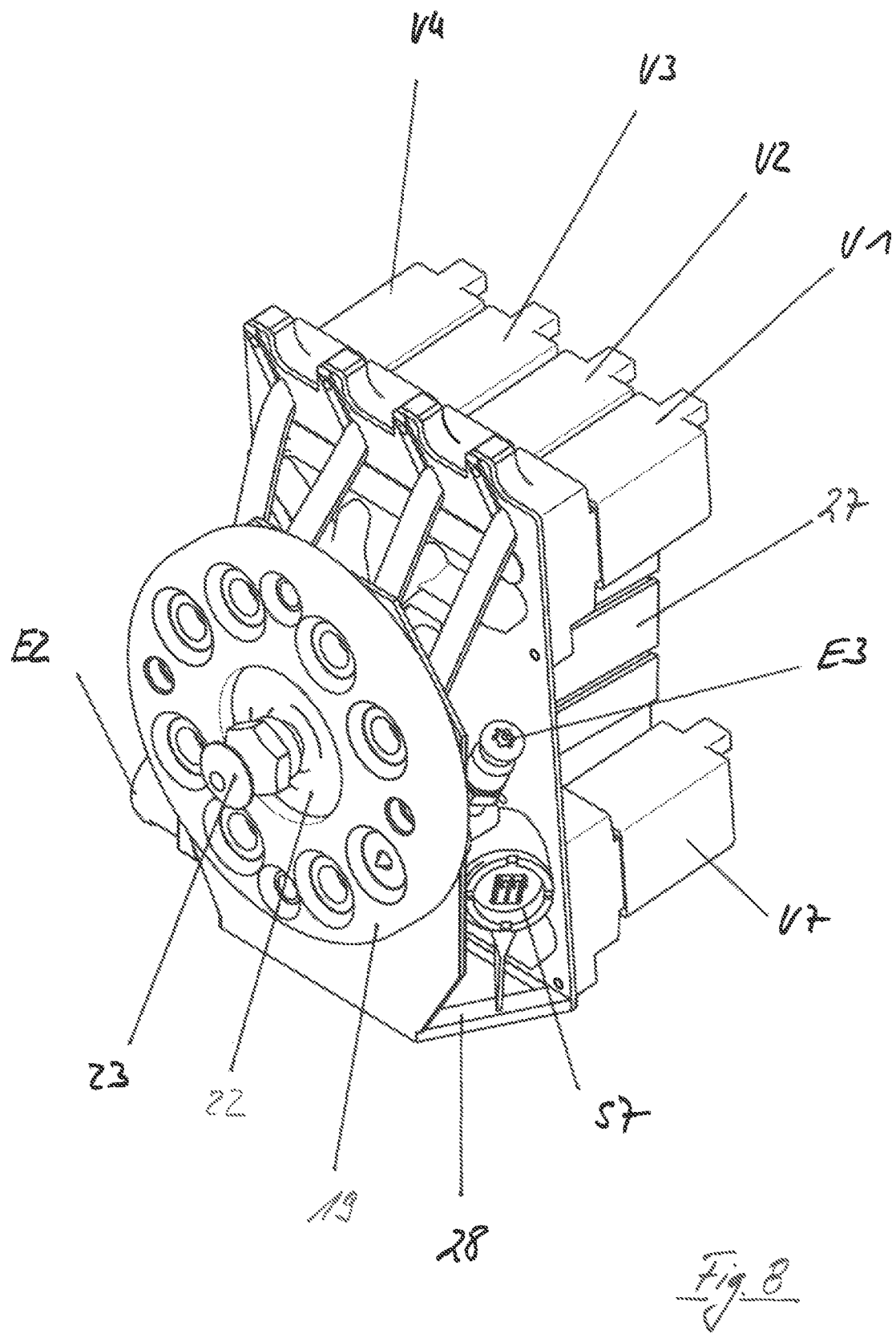

MODULE FOR APPLYING A MEDIUM TO ITEMS TO BE WASHED

CROSS-REFERENCE TO PRIOR APPLICATION

This application is a U.S. National Phase application under 35 U.S.C. § 371 of International Application No. PCT/EP2022/062603, filed on May 10, 2022, and claims benefit to German Patent Application No. DE 10 2021 113 274.6, filed on May 21, 2021. The International Application was published in German on Nov. 24, 2022 as WO/2022/243108 A1 under PCT Article 21(2).

FIELD

The invention relates to a module for applying a medium to narrow-bore ducts, conduits, pipes, and/or the like, of items to be washed, in particular endoscopes, which are disposed in a wash tub of a cleaning device, the module having a medium distribution device having a plurality of inlet-side ports and outlet-side ports, the inlet-side ports being in fluid connection with the outlet-side ports.

BACKGROUND

In the context of the invention, narrow-bore ducts, pipes, conduits, and/or the like, are ducts, pipes, conduits, and/or the like, that have a relatively small inner cross section: i.e., a relatively small inner diameter. This includes in particular medical instruments such as minimally invasive instruments, dental instruments, cannulas, catheters, endoscopes, and/or the like.

In order to clean narrow-bore ducts, pipes, conduits, and/or the like, it is known in the prior art to feed a cleaning liquid thereto. As a result of the cleaning liquid flowing through the narrow-bore ducts, pipes, conduits, and/or the like, any particles of dirt and/or foreign matter that may adhere to inner surface of the narrow-bore ducts, pipes, conduits, and/or the like, are removed.

For purposes of introducing cleaning liquid into narrow-bore ducts, pipes, conduits, and/or the like, the prior art has described a distribution chamber having an inlet-side port for a cleaning liquid as well as a plurality of outlet-side ports. During normal use, narrow-bore ducts, pipes, conduits, and/or the like, to be cleaned are respectively connected to the outlet-side ports of the distribution chamber.

To be able to further improve the cleaning result, it is also known in the art to pass not only cleaning liquid but also compressed air through the narrow-bore ducts, pipes, conduits, and/or the like, to be cleaned.

A module of the aforementioned type is described in DE 10 2018 121 450 A1.

The module known from DE 10 2018 121 450 A1 has a medium distribution device having a plurality of inlet-side ports and a plurality of outlet-side ports. The inlet-side ports are in fluid connection with the outlet-side ports, in each case with a valve interposed therebetween, allowing the outlet-side ports to be selectively fluidically connected to the inlet-side ports. The inlet-side ports available are a port for a cleaning liquid as well as two compressed air ports.

Although the module known from DE 10 2018 121 450 A1 has proven practical in everyday use, there is still a need for improvement, particularly with regard to an improved energy balance during a normal cleaning and/or disinfection process.

SUMMARY

In an embodiment, the present invention provides a module for applying a medium to narrow-bore ducts, conduits, pipes, and/or the like, of items to be washed, in particular endoscopes, which are disposed in a wash tub of a cleaning device, the module comprising: a medium distribution device having a plurality of inlet-side ports and outlet-side ports, the inlet-side ports being in fluid connection with the outlet-side ports: and a carrier flange having a push-pull cylinder, the push-pull cylinder being in fluid connection with an inlet-side port, and the push-pull cylinder providing a piston rod which is provided at an end thereof with an anchor that cooperates with a connecting device of a carrier for items to be washed.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following:

FIG. 6 is a schematic perspective view of a carrier flange of an inventive module according to a second embodiment:

FIG. 7 is a schematic perspective rear view of the carrier flange of FIG. 6;

FIG. 8 is a schematic perspective view of the inventive module according to a second embodiment:

DETAILED DESCRIPTION

Figure 1:
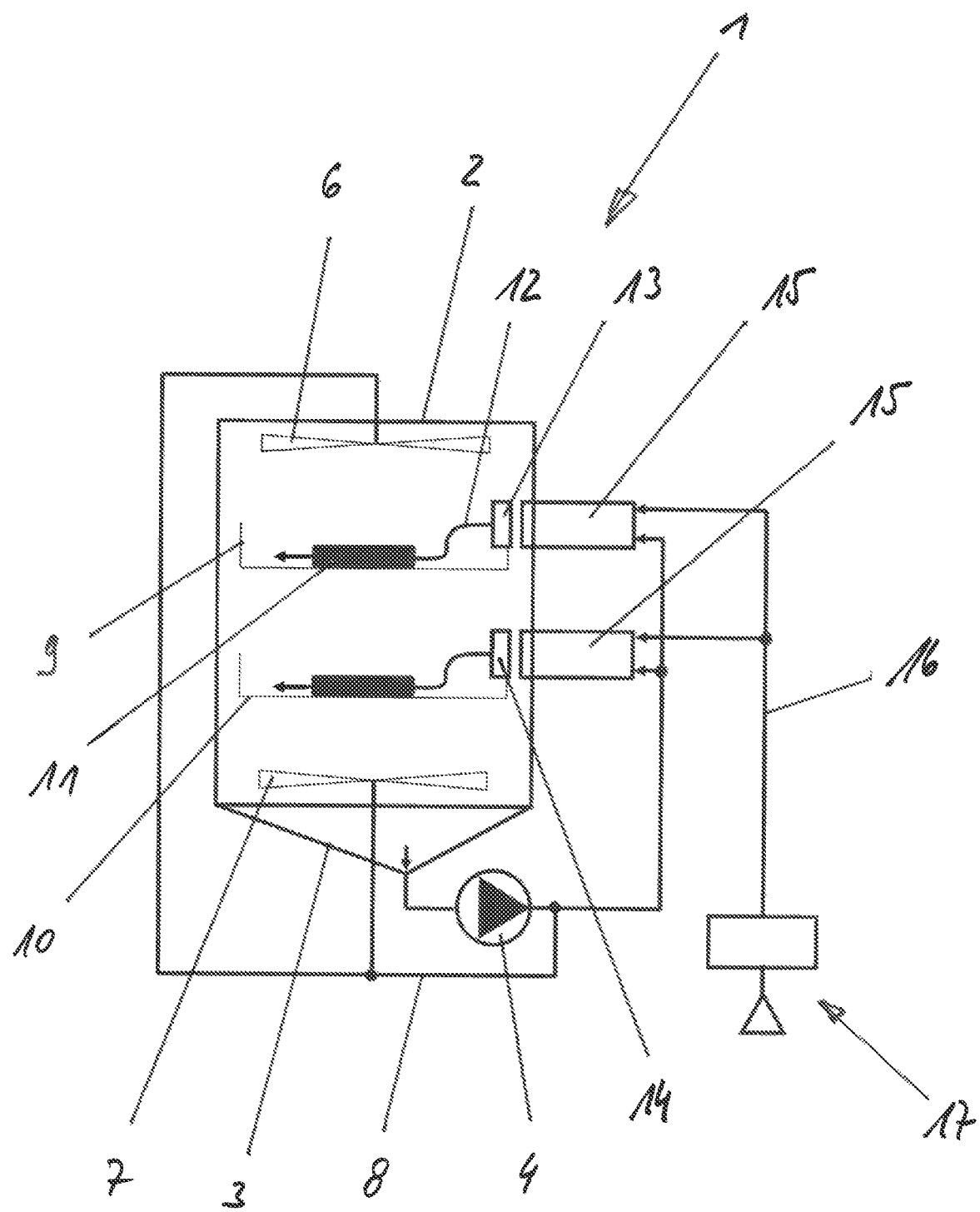
FIG. 1 is a schematic view of a cleaning device according to the invention.

In an embodiment, the present invention improves the design of a module of the above-mentioned type so as to allow for a more energy-efficient operation of a cleaning device equipped therewith.

In an embodiment, the present invention provides a module of the above-mentioned type which is characterized by a carrier flange having a push-pull cylinder, the push-pull cylinder being in fluid connection with an inlet-side port, and the push-pull cylinder providing a piston rod which is provided at an end thereof with an anchor that cooperates with a connecting device of a carrier for items to be washed. The invention further provides a cleaning device equipped with such a module.

The inventive module fluidically interconnects inlet-side ports and outlet-side ports in a generally known manner. In addition, it provides a carrier flange having a push-pull cylinder which, during normal use, serves for coupling to a connecting device of a carrier for items to be washed. For this purpose, during normal use, the push-pull cylinder is operated via a medium of one of the inlet-side ports. Therefore, the invention provides for the push-pull cylinder to be in fluid connection with an inlet-side port.

Thus, the module according to the invention not only enables supply of cleaning liquid and/or compressed air to the items to be washed and cleaned, but also provides a coupling function, so that, unlike in the prior art, no additional components or devices are needed for this purpose. Thus, the module according to the invention provides a functional unit which, during normal use, both provides for supply of medium and allows a connecting device of the cleaning device to be fluidically coupled to the outlet-side ports of the module.

This integration of functions into a single unit brings about a variety of advantages. During normal use, a shorter process time during treatment is achieved because the amount of cleaning liquid present in the wash circuit is reduced by the lack of additional hosing, which is associated with shorter heating, water intake, and water discharge processes. This reduces the amount of energy required for the heating processes for heating the cleaning liquid present in the wash circuit. In addition, assembly can be accomplished significantly faster since, unlike in the prior art, many assembly steps can be eliminated, especially those required for the placement of hose connections. This is because the design according to the invention eliminates the need for hose connections to fluidically connect the inventive module to a cleaning device.

Preferably, the carrier flange is manufactured by an additive manufacturing process, a machining process, or by primary shaping. In particular, the carrier flange may be manufactured by a 3D printing process, special preference being given to selective laser melting of metal, in particular stainless steel.

The push-pull cylinder of the inventive module has a piston rod. This piston rod has an anchor at an end thereof. The anchor in turn cooperates with a connecting device of a carrier for items to be washed, so that a stroke movement of the push-pull cylinder will cause either coupling or decoupling. Advantageously, no separate drive is needed to operate the push-pull cylinder since, in accordance with the invention, it is provided for the push-pull cylinder to be in fluid connection with an inlet-side port. This inlet-side port can thus be used not only to serve a medium to one or more outlet-side ports but also to cause the push-pull cylinder to operate as intended. In this way, advantageously, an overall compact design is achieved for the module which, without additional components and/or drives, is equipped to provide for the supply of medium to the outlet-side ports and to enable coupling to and decoupling from a coupling device of the cleaning device in the intended manner.

Thus, overall, a module is provided that enables simplified assembly, shorter process times, and, in addition, ensures a more energy-efficient operation.

Another feature of the invention provides for the push-pull cylinder to be a pneumatic cylinder. Therefore, a compressed air operated cylinder is used that is connected to an inlet-side port for compressed air. The push-pull cylinder can thus be charged with compressed air as needed via the inlet-side port.

In accordance with a further feature of the invention, the pneumatic cylinder is a pressure cylinder. During normal use, the cylinder is charged with compressed air such that, in order to couple the piston rod to the connecting device cooperating therewith, the piston rod moves away from the connecting device, and the anchor provided by the piston rod thus acts as a pull-type anchor. This ensures a reliable connection of the connecting device and the module according to the invention.

In accordance with another feature of the invention, the pressure cylinder is a double-acting pressure cylinder. The pressure cylinder therefore has two compressed air ports so that when charged via one port, the piston rod moves in one direction, whereas when the cylinder is charged via the other port, the piston rod moves in the opposite direction. Thus, both coupling and decoupling can occur under the action of compressed air. This ensures low-wear and reliable operation over the long term.

A further feature of the invention provides for a first inlet-side port to be a port for a cleaning liquid. During normal use, cleaning liquid: i.e., wash liquid, is pumped through this port and delivered to one or more outlet-side ports.

Another feature of the invention provides for a second inlet-side port to be a port for compressed air at a first pressure level of preferably below 2 bar. The compressed air at this pressure level is used, in particular, to be passed through the narrow-bore ducts, pipes, conduits, and/or the like, to be cleaned, optionally in interaction with the cleaning liquid. Therefore, the compressed air is at a pressure level that is preferably not above 2 bar in order to be able to reliably prevent accidental damage to the narrow-bore ducts, pipes, conduits, and/or the like, to be cleaned.

A further feature of the invention provides for a third inlet-side port to be a port for compressed air at a second pressure level of preferably below 500 mbar. This compressed air port is used, in particular, to enable leak testing and, therefore, this port is in fluid connection with an outlet-side port to which is fluidically connected a leakage tester.

Another feature of the invention provides for a fourth inlet-side port to be a port for compressed air at a third pressure level of preferably between 3 bar and 8 bar. This compressed air port is, in particular, in fluid connection with one of the outlet-side ports and with the push-pull cylinder. This allows this one outlet-side port to be selectively charged with cleaning liquid or with compressed air at a relatively high pressure level: i.e., at a pressure level above 2 mbar. In addition, this compressed air port is used to pressurize the push-pull cylinder, thus allowing it to be moved.

In accordance with a further feature of the invention, there is provided an outlet-side port which is fluidically connected to an upstream valve for selective connection to the first or the second inlet-side port. Such an outlet-side port can be selectively charged with cleaning liquid or with compressed air at preferably below 2 bar.

In accordance with another feature of the invention, there is provided an outlet-side port which is fluidically connected to an upstream valve for selective connection to the second or the fourth inlet-side port. This outlet-side port can be selectively charged with cleaning liquid or with compressed air at preferably between 3 bar and 5 bar.

In accordance with a further feature of the invention, there is provided an outlet-side port which is in fluid connection with the third inlet-side port. This outlet-side port can thus be charged with compressed air at preferably below 500 mbar for test purposes as needed.

A further feature of the invention provides for a housing of the push-pull cylinder to carry sensors on its outside for detecting the position of the piston rod. These sensors may be, for example, electromagnetic switches. The position detection for the piston rod makes it possible, in particular, to determine whether an adapter element, in particular in the form of an adapter plate, is used for coupling the pull-type anchor to a connecting device.

FIG. 1 shows in schematic form a cleaning device 1 which, in the exemplary embodiment shown, is an automated cleaner and/or disinfector.

Cleaning device 1 has a wash tub 2 providing a wash chamber for receiving items 11 to be washed and cleaned.

Carriers 9 and 10 for items to be washed are movably disposed within the wash chamber. In the exemplary embodiment shown, these carriers are washer racks. Each carrier 9 or 10 for items to be washed provides a connecting device 13, 14 to which is connected a narrow-bore duct 12 to be cleaned of an item 11 to be washed.

Disposed within wash tub 2 is a spray device for applying cleaning liquid, also called wash liquid, to the exterior surface of the item 11 to be washed. In the exemplary embodiment shown, the spray device has two rotating spray arms 6 and 7.

Wash tub 2 empties into a collection sump 3. Collection sump 3 is in turn fluidically connected to a recirculation pump 4, which is in fluid connection with the spray arms 6 and 7 of the spray device via a conduit 8. During normal use, wash liquid is delivered through spray arms 6 and 7 for exterior cleaning of the item 11 to be washed. The wash liquid then collects in collection sump 3, from where it is fed back to spray arms 6 and 7 by recirculation pump 4 and is thus circulated in the loop. For interior cleaning of the item 11 to be washed, and especially of narrow-bore ducts 12, recirculation pump 4 is, in addition, fluidically connected to connecting devices 13 and 14, in each case with an inventive module 15 interposed therebetween.

Modules 15 are further connected via a compressed air conduit 16 to a compressed air source 17. This allows modules 15 to be charged with both wash liquid and compressed air, which makes it possible to pass either wash liquid or compressed air through the narrow-bore ducts 12 of the item 11 to be washed.

Figure 2:
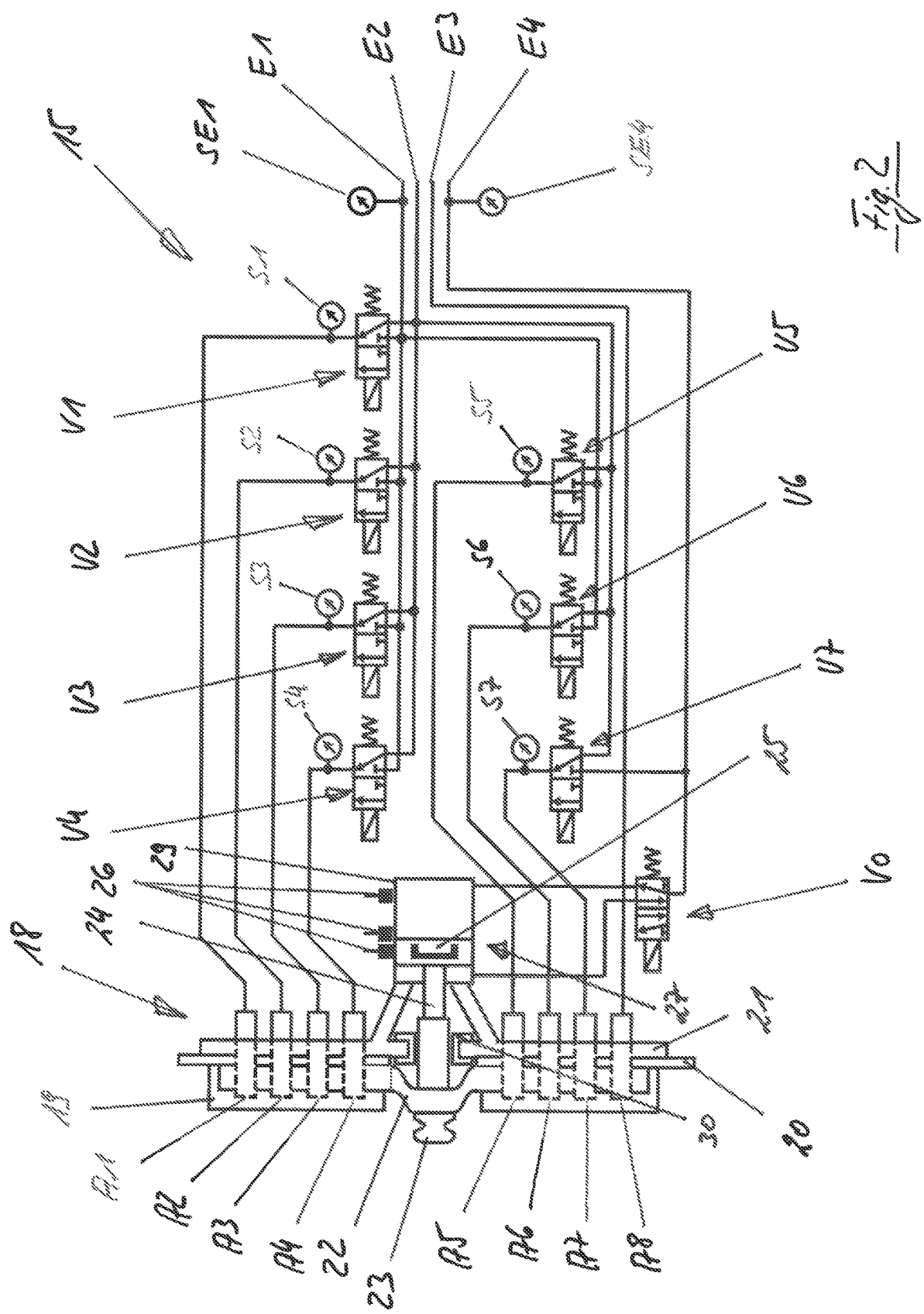
FIG. 2 is a schematic circuit diagram of a module according to the invention.

The design of an inventive module 15 is illustrated in FIG. 2 in a schematic circuit diagram.

As can be seen from FIG. 2, a module 15 has a medium distribution device having a plurality of inlet-side ports E1, E2, E3 and E4 as well as a plurality of outlet-side ports A1, A2, A3, A4, A5, A6, A7 and A8. First inlet-side port E1 is a port for wash liquid. Each of the other inlet-side ports E2, E3, and E4 is a port for compressed air. Second inlet-side port E2 provides a port for compressed air at a first pressure level of preferably below 2 bar, third inlet-side port E2 provides a port for compressed air at a second pressure level of preferably below: 500 mbar, and fourth inlet-side port E4 provides a port for compressed air at a third pressure level of preferably between 3 bar and 5 bar. Each of the inlet-side ports E1 through E4 may be associated with an inlet pressure sensor SE1 through SE4.

Valves V1 through V7 are provided for selectively charging outlet-side ports A1 through A7 with wash liquid and/or compressed air. More particularly, outlet-side ports A1 through A6 are fluidically connected to upstream valves V1 through V6 so that each of the outlet-side ports A1 through A6 can be selectively charged with wash liquid via inlet-side port E1 or with compressed air at a pressure level of preferably below 2 bar via the second inlet-side port E2. During normal use, each of these outlet-side ports A1 through A6 may have connected thereto the narrow-bore duct 12 of an item 11 to be washed.

Valve 7 is connected upstream of outlet-side port A7 in series therewith. Valve 7 is in fluid connection with inlet-side ports E2 and E4. Outlet-side port A7 can thus be selectively charged either with compressed air at a pressure level of preferably below 2 bar or with compressed air at a pressure level of preferably between 3 bar and 5 bar.

Outlet-side port A8 is connected directly to inlet-side port E3 without a valve interposed therebetween, which allows this outlet-side port to be charged with compressed air at a second pressure level of preferably below 500 mbar.

Each of the valves V1 through V7 has a pressure sensor S1 through S7 connected downstream thereof.

For purposes of coupling module 15 to a connecting device 13 or 14 provided on a carrier for items to be washed, module 15 has a push-pull cylinder 27. Push-pull cylinder 27 has a piston guided in a housing 29. Piston 25 is connected to a piston rod 24 carrying an anchor 23 at an end thereof.

In the exemplary embodiment shown, push-pull cylinder 27 is designed as a double-acting pressure cylinder and connected to fourth inlet-side port E4 with the valve V0 interposed therebetween. This allows push-pull cylinder 24 to be charged with compressed air at a pressure level of preferably between 3 bar and 5 bar.

In the exemplary embodiment shown, three electromagnetic switches 26 are disposed on the outside of housing 29 of push-pull cylinder 27, enabling determination of the position of the piston. This makes it possible to detect whether an optional adapter plate is connected to anchor 23.

A carrier flange 18 is provided for attachment of a module 15 to the wash tub 2 of a cleaning device 1. Carrier flange 18 has a connecting plate 19 and a counter-plate 21 which, in the final assembled state, receive wall 20 of wash tub 2 therebetween. A seal 22 is provided to provide sealing from the wash chamber provided by wash tub 2. In addition, carrier flange 18 provides the bearing 30 for mounting piston rod 24 of push-pull cylinder 27 in a longitudinally movable manner.

Figure 3:
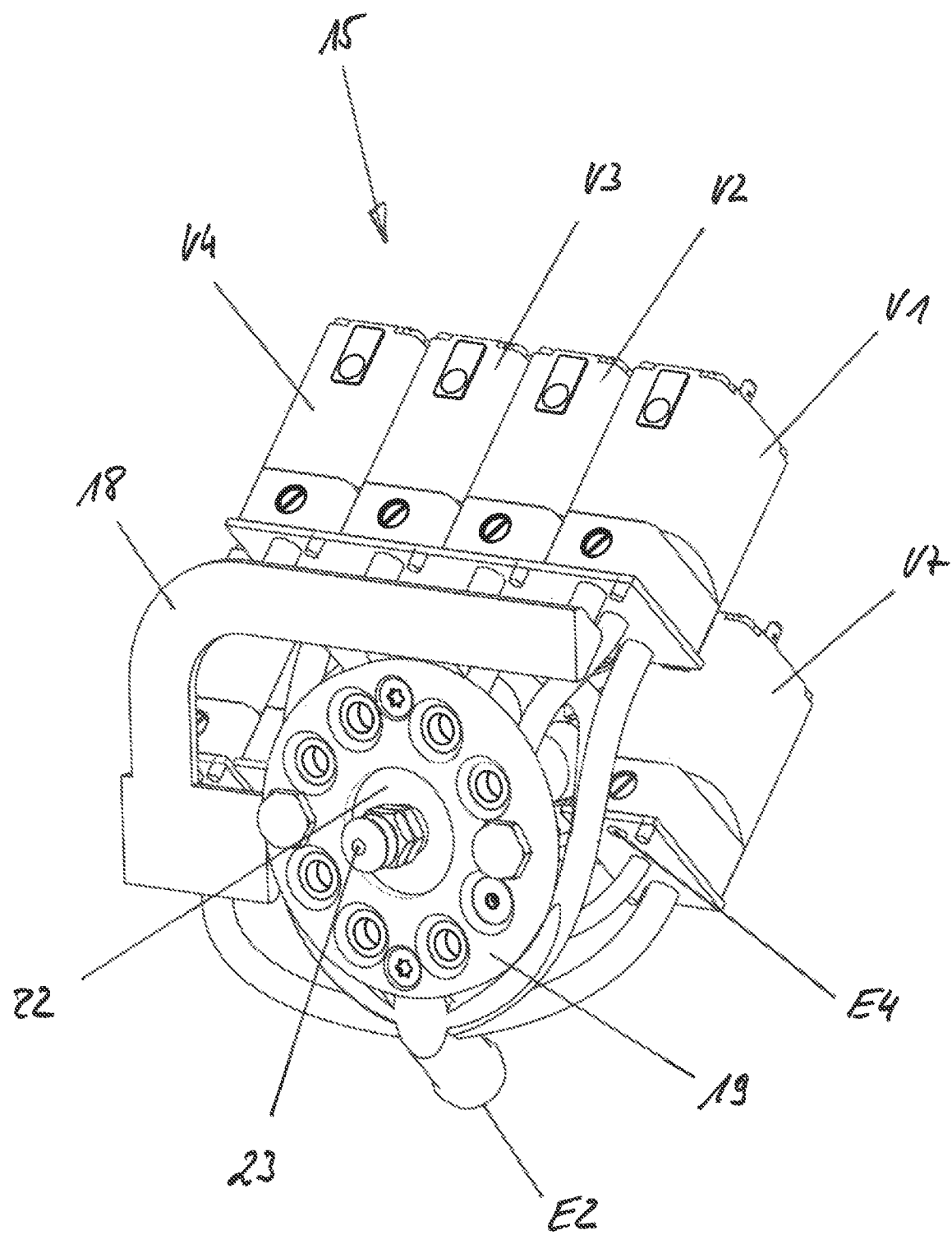
FIG. 3 is a schematic perspective view of an inventive module according to a first embodiment.
Figure 4:
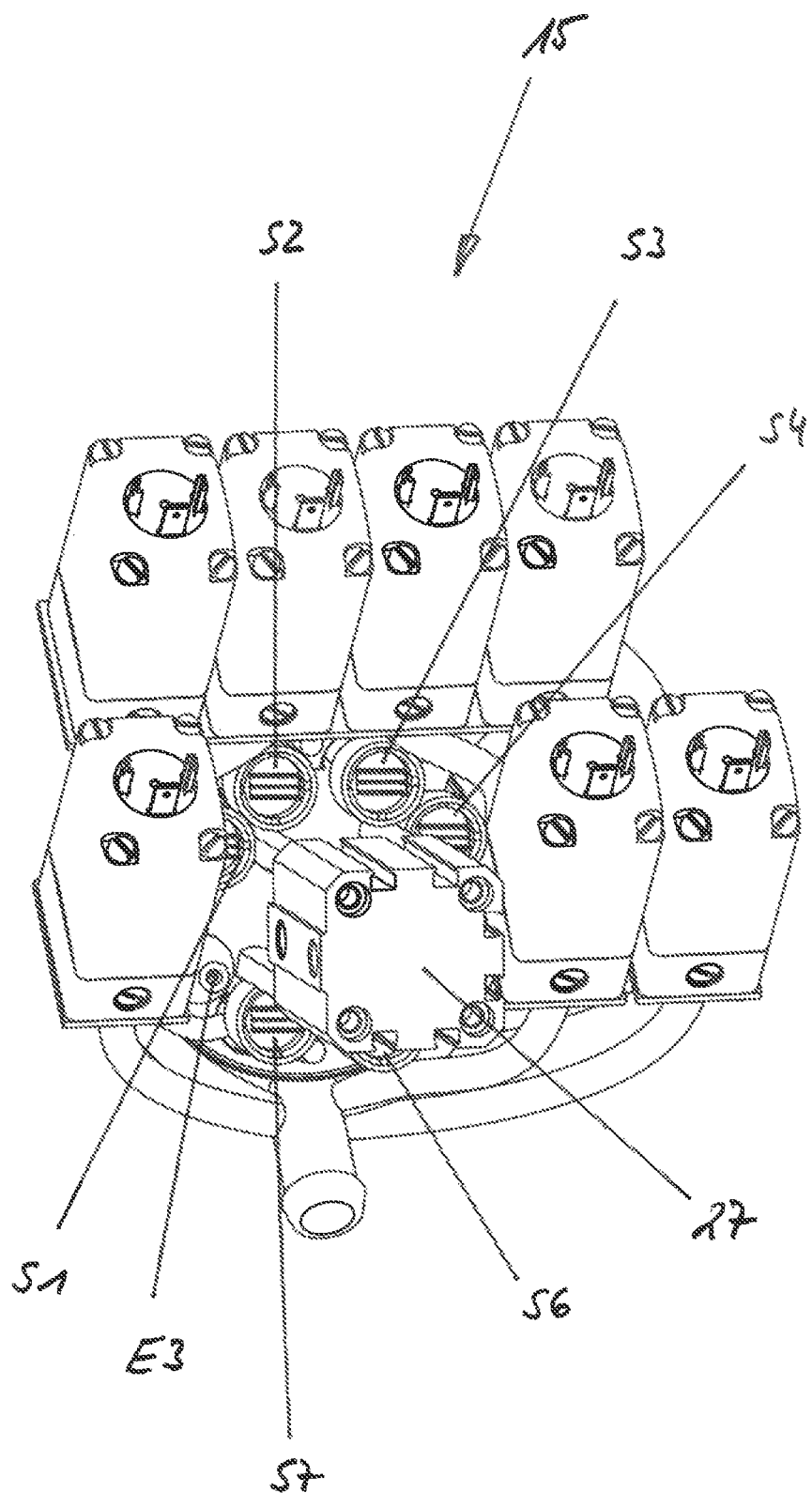
FIG. 4 is a schematic perspective view of the inventive module of FIG. 3.
Figure 5:
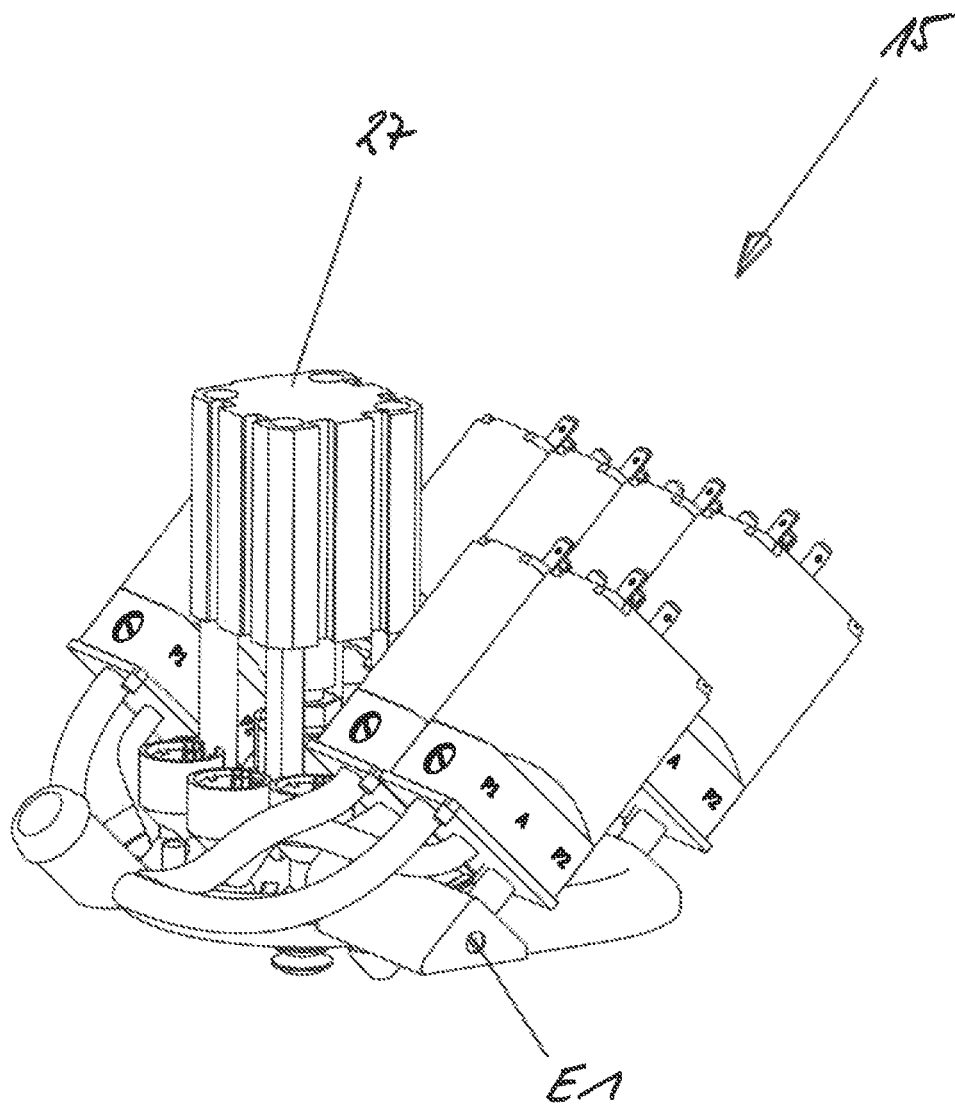
FIG. 5 is a schematic perspective view of the inventive module of FIGS. 3 and 4.

FIGS. 3 through 5 are different perspective views of an inventive module 15 according to a first embodiment. These views illustrate in particular the arrangement of valves V1 through V7 as well as the arrangement of push-pull cylinder 27.

FIGS. 6 through 10 show a second embodiment of a module 15 according to the invention. This embodiment differs from the embodiment of FIGS. 3 through 5 in particular in the design of carrier flange 18. However, the working principle is the same as described above.

In both embodiments shown, the carrier flange may be manufactured in a 3D printing process, special preference being given to selective laser melting of metal, in particular stainless steel.

The inventive module 15 is characterized in particular by its pneumatic-cylinder-based coupling function. Overall, therefore, a compact design is achieved, where module 15 enables coupling to an associated connecting device 13 or 14 and, in addition, provides for selective application of wash liquid and/or compressed air to outlet-side ports A1 through A7 via inlet-side ports E1 through E4.

The two end positions of piston rod 24 can be detected via the electromagnetic switches 26 attached to the outside of housing 29 of push-pull cylinder 27, which makes it possible to distinguish between a coupled state and a decoupled state of module 15. Furthermore, a third electromagnetic switch 26 can be used to detect whether an adapter plate is connected to anchor 23. This third electromagnetic switch is attached to the cylinder at the position where the adapter plate is normally pulled into the seal via the anchor.

With regard to push-pull cylinder 27, conventional Hooke-type spring elements, such as tension and compression springs, can advantageously be dispensed with since a uniform force that is independent of the traveled path is achieved via the inlet-side port E4 and the piston or piston ring surface of push-pull cylinder 27.

Figure 9:
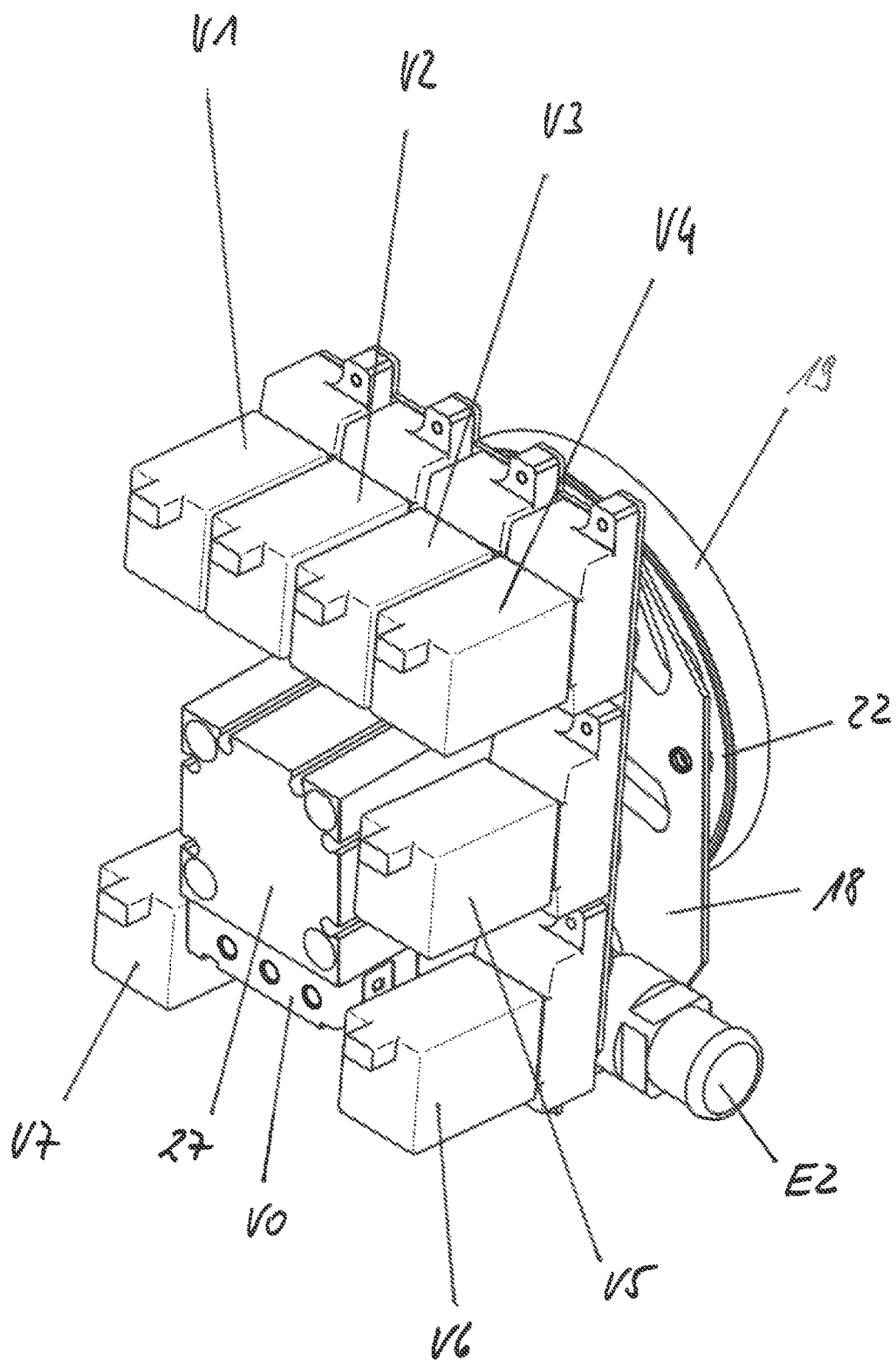
FIG. 9 is a schematic perspective view of the inventive module of FIG. 8.
Figure 10:
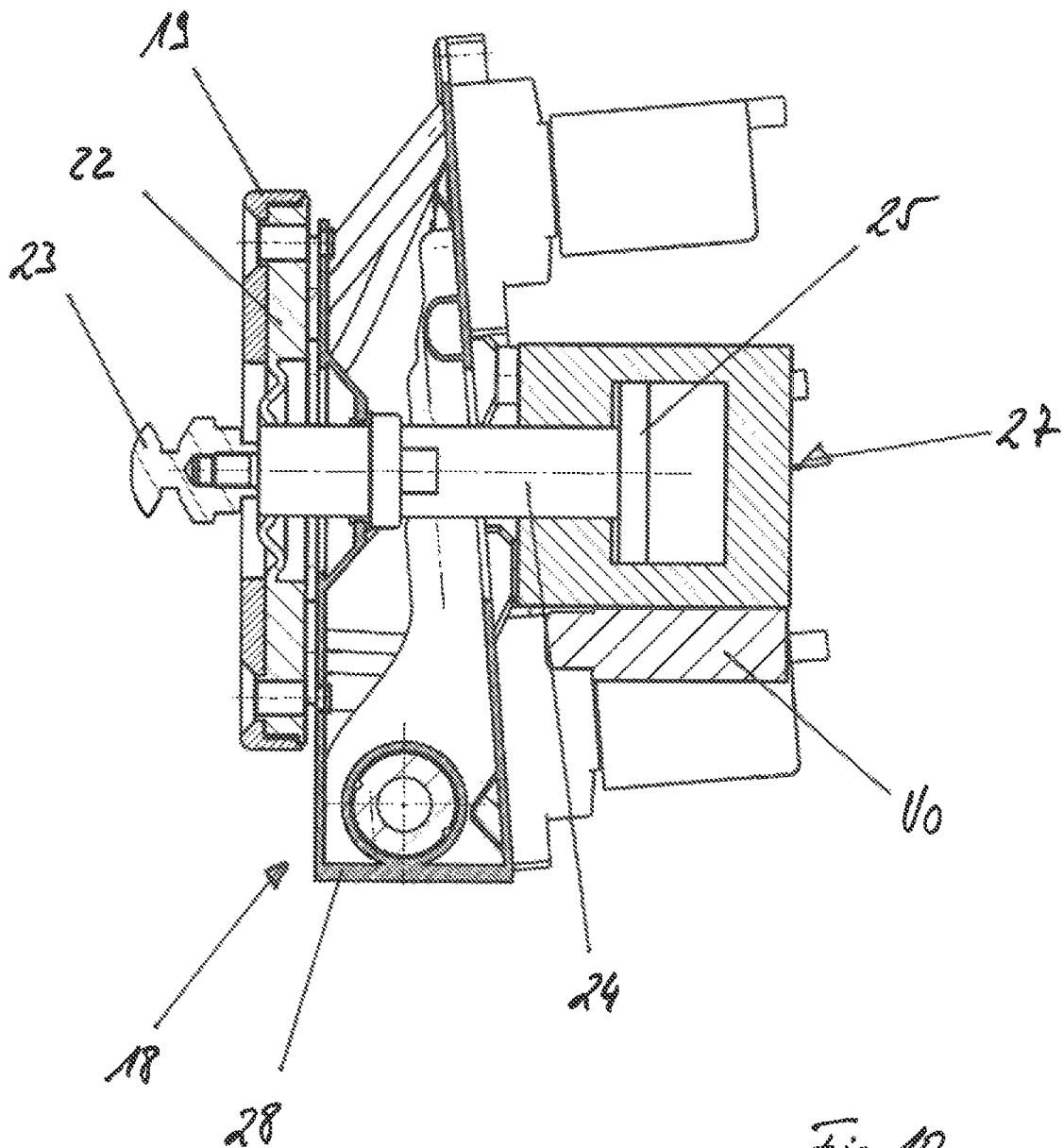
FIG. 10 is a schematic sectional view of the inventive module of FIGS. 8 and 9.

In the embodiment shown in FIGS. 6 through 10, a carrier flange 18 manufactured in a 3D printing process and having a main body 28 is used. In the final assembled state, valves V0 through V7 and push-pull cylinder 27 are mounted on main body 28, as illustrated in FIGS. 8 and 9. Thus, an overall compact design is achieved.

The combination of the functions of the medium distribution device and of the mechanism for coupling to a connecting device provided on a carrier for items to be washed not only results in an overall more robust and smaller design but also achieves the following features:

less water required for treatment processes
less energy required for heating the volume of water
shorter heating phases due to the small amount of energy required
faster water exchange processes due to smaller water volumes in each wash step
faster treatment processes due to shorter heating phases and water exchange processes
reduction of the assembly time due to fewer components and hoses.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE CHARACTERS 1 cleaning device
2 wash tub
3 collection sump
4 recirculation pump
6 spray arm
7 spray arm
8 conduit
9 carrier for items to be washed
10 carrier for items to be washed
11 item to be washed
12 duct
13 connecting device
14 connecting device
15 module
16 compressed air conduit
17 compressed air source
18 carrier flange
19 connecting plate
20 wash tub wall
21 counter-plate
22 seal
23 anchor
24 piston rod
25 piston
26 electromagnetic switch
27 push-pull cylinder
28 main body
29 housing
30 bearing
E1 through E4 inlet-side port
A1 through A8 outlet-side port
SE1 through SE4 sensor, inlet-side port E1 through E4
S1 through S7 pressure sensor
V0 through V7 valve

The invention claimed is:

1. A module for applying a medium to narrow-bore ducts, conduits, and/or pipes, of items to be washed, which are disposed in a wash tub of a cleaning device, the module comprising:
   a medium distribution device having a plurality of inlet-side ports and outlet-side ports, the inlet-side ports being in fluid connection with the outlet-side ports; and
   a carrier flange having a push-pull cylinder, the push-pull cylinder being in fluid connection with an inlet-side port, and the push-pull cylinder providing a piston rod which is provided at an end thereof with an anchor that cooperates with a connecting device of a carrier for items to be washed.

2. The module of claim 1, wherein the push-pull cylinder comprises a pneumatic cylinder.

3. The module of claim 2, wherein the pneumatic cylinder comprises a pressure cylinder.

4. The module of claim 3, wherein the pressure cylinder comprises a double-acting pressure cylinder.

5. The module of claim 1, wherein a first inlet-side port comprises a port for a cleaning liquid.

6. The module of claim 5, wherein a second inlet-side port comprises a port for compressed air-at a first pressure level.

7. The module of claim 6, wherein the first pressure level is below 2 bar.

8. The module of claim 6, wherein a third inlet-side port comprises a port for compressed air at a second pressure level.

9. The module of claim 8, wherein the second pressure level is below 500 mbar.

10. The module of claim 8, wherein a fourth inlet-side port comprises a port for compressed air at a third pressure level.

11. The module of claim 10, wherein the third pressure level is between 3 bar and 5 bar.

12. The module of claim 10, wherein the push-pull cylinder is in fluid connection with the fourth inlet-side port.

13. The module of claim 1, wherein a housing of the push-pull cylinder carries sensors on an outside thereof for detecting a position of the piston rod.

14. The module of claim 13, wherein the sensors comprise electromagnetic switches.

15. The module of claim 6, further comprising:
an outlet-side port which is fluidically connected to an upstream valve for selective connection to the first inlet-side port or the second inlet-side port.

16. The module of claim 10, further comprising:
an outlet-side port which is fluidically connected to an upstream valve for selective connection to the second or the fourth inlet-side port.

17. The module of claim 8, further comprising:
an outlet-side port which is in fluid connection with the third inlet-side port.

18. The module of claim 1, wherein the items to be washed comprise endoscopes.

19. A cleaning device, comprising:
a wash tub that provides a wash chamber for receiving items to be washed and cleaned; and
the module of claim 1.

20. The cleaning device of claim 19, wherein the cleaning device comprises an automated cleaner and/or disinfector.

* * * * *